US011285487B2

(12) United States Patent
Hoffmann, Jr. et al.

(10) Patent No.: US 11,285,487 B2
(45) Date of Patent: Mar. 29, 2022

(54) TIP RESISTANT OPTICAL TESTING INSTRUMENT

(71) Applicant: bioMerieux, Inc., Durham, NC (US)

(72) Inventors: Jack R. Hoffmann, Jr., St. Louis, MO (US); Gregory R. Maes, Fenton, MO (US)

(73) Assignee: bioMerieux, Inc., Durham, NC (US)

( * ) Notice: Subject to any disclaimer, the term of this patent is extended or adjusted under 35 U.S.C. 154(b) by 835 days.

(21) Appl. No.: 15/958,777

(22) Filed: Apr. 20, 2018

(65) Prior Publication Data

US 2018/0304255 A1 Oct. 25, 2018

Related U.S. Application Data

(60) Provisional application No. 62/488,450, filed on Apr. 21, 2017, provisional application No. 62/487,796, (Continued)

(51) Int. Cl.
*G01N 21/01* (2006.01)
*B01L 3/00* (2006.01)
(Continued)

(52) U.S. Cl.
CPC .......... *B01L 3/50853* (2013.01); *G01N 1/10* (2013.01); *G01N 15/06* (2013.01); *G01N 21/01* (2013.01);
(Continued)

(58) Field of Classification Search
CPC .............. G01N 21/01; G01N 21/251; G01N 2021/0106; G01N 2021/0112
See application file for complete search history.

(56) References Cited

U.S. PATENT DOCUMENTS 2,157,438 A 5/1939 Sparks
2,436,262 A 2/1948 Miller
(Continued)

FOREIGN PATENT DOCUMENTS

CN 3159492 1/2000
CN 3383938 11/2003
(Continued)

OTHER PUBLICATIONS

International Search Report and Written Opinion for Application No. PCT/US2018/028699 dated Jul. 16, 2018, 14 pages.
(Continued)

*Primary Examiner* — Jill A Warden
*Assistant Examiner* — Dwayne K Handy
(74) *Attorney, Agent, or Firm* — Alston & Bird LLP

(57) ABSTRACT

Apparatuses and associated methods of manufacturing are described that provide a tip resistant optical testing instrument configured to rest on a surface. The optical testing instrument includes a shell defining a cavity for receiving a sample tube. The shell includes a bottom shell surface, wherein the bottom shell surface defines at least one support element, wherein the at least one support element is configured to engage the surface to support the optical testing instrument in a testing position, and a translational surface configured to engage the surface to support the optical testing instrument in an angled position. In an instance in which the optical testing instrument tilts from the testing position to the angled position, the translational surface is configured to engage the surface contacting the translational surface to prevent the optical testing instrument from tipping further and allow the optical testing instrument to return to the testing position.

24 Claims, 5 Drawing Sheets

Related U.S. Application Data filed on Apr. 20, 2017, provisional application No. 62/487,807, filed on Apr. 20, 2017, provisional application No. 62/487,736, filed on Apr. 20, 2017, provisional application No. 62/487,860, filed on Apr. 20, 2017.

(51) Int. Cl.

| | |
|---|---|
| *G01N 21/59* | (2006.01) |
| *G01N 21/47* | (2006.01) |
| *G01N 1/10* | (2006.01) |
| *G01N 21/27* | (2006.01) |
| *G01N 33/487* | (2006.01) |
| *G01N 21/03* | (2006.01) |
| *G01N 15/06* | (2006.01) |
| *G01N 21/51* | (2006.01) |
| *G01N 21/88* | (2006.01) |
| *G01N 21/93* | (2006.01) |

(52) U.S. Cl.
CPC ....... *G01N 21/0303* (2013.01); *G01N 21/274* (2013.01); *G01N 21/4738* (2013.01); *G01N 21/4785* (2013.01); *G01N 21/51* (2013.01); *G01N 21/5907* (2013.01); *G01N 21/8806* (2013.01); *G01N 21/93* (2013.01); *G01N 33/487* (2013.01); *G01N 33/48735* (2013.01); *B01L 2200/14* (2013.01); *B01L 2300/0654* (2013.01); *B01L 2300/0803* (2013.01); *B01L 2300/12* (2013.01); *G01N 21/474* (2013.01); *G01N 2015/0693* (2013.01); *G01N 2021/0168* (2013.01); *G01N 2021/0389* (2013.01); *G01N 2021/4769* (2013.01); *G01N 2021/598* (2013.01); *G01N 2201/126* (2013.01); *G01N 2201/12707* (2013.01)

(56) References Cited

U.S. PATENT DOCUMENTS

| | | | |
|---|---|---|---|
| 2,863,354 | A | 12/1958 | Diehl et al. |
| 2,874,606 | A | 2/1959 | Leiterer |
| 3,554,648 | A | 1/1971 | Boostrom et al. |
| 3,712,144 | A | 1/1973 | Kuzel et al. |
| 3,714,445 | A | 1/1973 | Blachere et al. |
| 3,775,013 | A | 11/1973 | Simms |
| 3,783,635 | A | 1/1974 | Perez |
| 3,809,912 | A | 5/1974 | Henning |
| 3,826,574 | A | 7/1974 | Brown, Jr. |
| 3,962,041 | A | 6/1976 | Muller et al. |
| 3,977,794 | A | 8/1976 | Liedholz |
| 4,118,625 | A | 10/1978 | Underwood |
| 4,193,692 | A | 3/1980 | Wynn |
| 4,291,983 | A | 9/1981 | Kraft et al. |
| 4,343,552 | A | 8/1982 | Blades |
| 5,137,693 | A | 8/1992 | Mawhirt |
| 5,140,168 | A | 8/1992 | King |
| 5,331,177 | A | 7/1994 | Kunisiak et al. |
| 5,506,679 | A * | 4/1996 | Cooper ................. G01N 21/53 356/338 |
| 5,604,590 | A | 2/1997 | Cooper et al. |
| 5,616,923 | A | 4/1997 | Rich et al. |
| 5,651,941 | A | 7/1997 | Stark et al. |
| 5,687,849 | A | 11/1997 | Borenstein et al. |
| 5,736,410 | A | 4/1998 | Zarling et al. |
| 5,863,754 | A | 1/1999 | Bajard |
| 5,867,266 | A | 2/1999 | Craighead |
| 5,872,361 | A | 2/1999 | Paoli et al. |
| 5,940,178 | A | 8/1999 | Barber et al. |
| D439,673 | S | 3/2001 | Brophy et al. |
| 6,198,536 | B1 * | 3/2001 | Baker ................. G01J 3/50 250/226 |
| 6,274,092 | B1 | 8/2001 | Itoh |
| D453,573 | S | 2/2002 | Lafond et al. |
| 6,359,689 | B1 | 3/2002 | Stansell et al. |
| 6,537,772 | B1 | 3/2003 | Alarcon et al. |
| 7,485,264 | B2 | 2/2009 | Itoh |
| 7,659,980 | B1 | 2/2010 | Mitchell et al. |
| D624,194 | S | 9/2010 | Pack et al. |
| 7,910,067 | B2 | 3/2011 | Knight et al. |
| 8,147,777 | B2 | 4/2012 | Schacher et al. |
| D679,412 | S | 4/2013 | Khamu |
| D687,567 | S | 8/2013 | Jungheim et al. |
| D709,625 | S | 7/2014 | Baum et al. |
| 2003/0005928 | A1 | 1/2003 | Appel et al. |
| 2003/0058450 | A1 | 3/2003 | Mosley et al. |
| 2003/0008522 | A1 | 5/2003 | Smolenski et al. |
| 2003/0139886 | A1 | 7/2003 | Bodzin et al. |
| 2004/0147843 | A1 | 7/2004 | Bambot et al. |
| 2005/0106746 | A1 | 5/2005 | Shinn et al. |
| 2006/0001865 | A1 | 1/2006 | Bellalou et al. |
| 2007/0269853 | A1 | 11/2007 | Galiano |
| 2008/0072664 | A1 | 3/2008 | Hansen et al. |
| 2008/0079943 | A1 | 4/2008 | Li |
| 2010/0028859 | A1 | 2/2010 | Moshe et al. |
| 2010/0110220 | A1 | 5/2010 | Leugers et al. |
| 2010/0245827 | A1 | 9/2010 | Palumbo et al. |
| 2011/0151503 | A1 | 6/2011 | Galiano |
| 2011/0270128 | A1 | 11/2011 | Zhao et al. |
| 2011/0306032 | A1 | 12/2011 | Galiano et al. |
| 2011/0306087 | A1 | 12/2011 | Galiano et al. |
| 2011/0307183 | A1 | 12/2011 | Galiano et al. |
| 2012/0009558 | A1 | 1/2012 | Armstrong et al. |
| 2012/0022794 | A1 | 1/2012 | Andelic et al. |
| 2012/0063956 | A1 | 3/2012 | Truex et al. |
| 2012/0082446 | A1 | 4/2012 | Kumai |
| 2012/0140230 | A1 | 6/2012 | Miller |
| 2013/0022962 | A1 | 1/2013 | Galiano |
| 2013/0258336 | A1 | 10/2013 | Ostermeyer et al. |
| 2014/0233015 | A1 | 8/2014 | Mander |
| 2015/0031051 | A1 | 1/2015 | Mohan |
| 2015/0036121 | A1 | 2/2015 | Kurowski et al. |
| 2015/0086971 | A1 | 4/2015 | Branch et al. |
| 2015/0108076 | A1 | 4/2015 | Branch et al. |
| 2015/0355208 | A1 | 12/2015 | German |
| 2016/0160260 | A1 | 6/2016 | Marshall et al. |
| 2016/0266028 | A1 | 9/2016 | Wyatt |
| 2017/0307525 | A1 | 10/2017 | Langoff et al. |
| 2019/0162744 | A1 | 5/2019 | Kazama et al. |

FOREIGN PATENT DOCUMENTS

| | | |
|---|---|---|
| CN | 2919238 | 7/2007 |
| CN | 300905477 D | 12/2007 |
| CN | 201141824 | 10/2008 |
| CN | 301068253 | 11/2008 |
| CN | 204142554 | 2/2010 |
| CN | 101893564 A | 11/2010 |
| CN | 102128814 A | 7/2011 |
| CN | 103645162 A | 3/2014 |
| CN | 203479704 | 3/2014 |
| CN | 302968146 S | 6/2014 |
| CN | 302983583 S | 6/2014 |
| CN | 302995249 S | 6/2014 |
| CN | 103923827 | 7/2014 |
| CN | 303227067 S | 12/2014 |
| CN | 104266895 | 1/2015 |
| CN | 105277472 A | 1/2016 |
| CN | 205246536 U | 5/2016 |
| DE | 3516529 | 11/1986 |
| DE | 3608552 A1 | 9/1987 |
| DE | 202004020585 | 9/2005 |
| EP | 3023768 | 5/2016 |
| GB | 150 183 A | 9/1920 |
| GB | 4028381 | 1/2013 |
| GB | 4028382 | 1/2013 |
| JP | 3049676 | 6/1998 |
| JP | H10 284848 A | 10/1998 |
| JP | 3061144 | 9/1999 |
| JP | 2003/000224 | 1/2003 |
| KR | 100580312 | 5/2006 |
| KR | 20090081998 | 7/2009 |

(56) References Cited

FOREIGN PATENT DOCUMENTS

| | | |
|---|---|---|
| KR | 20090082060 | 7/2009 |
| KR | 100580313 | 5/2018 |
| TW | 201215873 A | 4/2012 |
| WO | WO 1993/009440 A1 | 5/1993 |
| WO | WO 1995/25950 A1 | 9/1995 |
| WO | WO 1998/000701 AI | 1/1998 |
| WO | WO 1998/047999 A1 | 10/1998 |
| WO | WO 2000/065332 A1 | 11/2000 |
| WO | WO 2001/063253 A1 | 8/2001 |
| WO | WO 2004/015136 A1 | 2/2004 |
| WO | WO 2008/039442 A1 | 4/2008 |
| WO | WO 2010/090391 A2 | 8/2010 |
| WO | WO 2010/097687 A1 | 9/2010 |
| WO | WO 2010/108804 A1 | 9/2010 |
| WO | WO 2014/137333 A1 | 9/2014 |
| WO | WO 2015/026794 A1 | 2/2015 |
| WO | WO 2015/164274 A1 | 10/2015 |
| WO | WO 2016/049604 A1 | 3/2016 |
| WO | WO 2016/051267 A1 | 4/2016 |
| WO | WO 2016/191646 A1 | 12/2016 |
| WO | WO 2018/195509 A1 | 10/2018 |

OTHER PUBLICATIONS

International Search Report and Written Opinion for Application No. PCT/US2018/028696 dated Sep. 7, 2018.
International Search Report and Written Opinion for Application No. PCT/US2018/028701 dated Sep. 10, 2018.
International Search Report and Written Opinion for Application No. PCT/US2018/028702 dated Sep. 10, 2018.
Office Action for European Application No. i 8724032,0 dated Jan. 28. 2021.
Office Action for Australian Patent Application No. 2018254602 dated Jan. 27, 2021.
Office Actionfor European Application No. 18724031.2 dated Oct. 7, 2021.
Office Action for Chinese Application No. 2018800328421 dated Nov. 18, 2021.

* cited by examiner

TIP RESISTANT OPTICAL TESTING INSTRUMENT

CROSS-REFERENCE TO RELATED APPLICATIONS

This application claims the benefit of each of the following: U.S. Provisional Application No. 62/487,860, which is entitled "Tip Resistant Optical Testing Instrument" and was filed Apr. 20, 2017; U.S. Provisional Application No. 62/487,807, which is entitled "Optical Test Platform" and was filed Apr. 20, 2017; U.S. Provisional Application No. 62/487,796, which is entitled "Optical Density Instrument And Systems And Methods Using The Same" and was filed Apr. 20, 2017; U.S. Provisional Application No. 62/488,450, which is entitled "Optical Density Instrument And Systems And Methods Using The Same" and was filed Apr. 21, 2017; and U.S. Provisional Application No. 62/487,736, which is entitled "Method, Apparatus, And Computer Program Product For Controlling Components Of A Detection Device" and was filed Apr. 20, 2017. Each of the foregoing applications is hereby incorporated by reference in its entirety.

BACKGROUND

In laboratory environments and other similar testing settings, lab technicians, scientists, students, and other practitioners often utilize various laboratory equipment to measure conditions of liquid suspensions or samples held within sample tubes, vials, or the like. These practitioners may utilize various devices or instruments to perform testing procedures on the liquid contained in the sample tube, and may further record any resulting measurements. In some instances, for example while performing a testing procedure, the practitioner may be required by the testing procedure to manipulate the fluid in order to achieve a particular result. In other instances, the practitioner may also intentionally or inadvertently move the testing instrument between procedures.

In any circumstance, movement of the testing instrument may result in the instrument accidently tipping over or falling. Any tipping of the testing instrument may also result in the spilling of the liquid samples contained within the sample tubes housed by the testing instrument. Due to the cost and time required to prepare the liquid samples and conduct the subsequent procedures, it is desired to prevent or otherwise resist the spilling of any liquid contained in sample tubes during movement of the testing instrument. Additionally, electrical damage to the instrument's internal components or damage to the sample tubes may result in the event the testing instrument tips over or falls. Further, traditional testing instruments are often incapable of preventing or resisting tipping of the testing instrument due to unstable base designs, poor weight distribution, and/or unsuitable material choice. The inventors have identified numerous other deficiencies with existing technologies in the field, the remedies for which are the subject of the embodiments described herein.

BRIEF SUMMARY

Accordingly, the apparatuses and methods described herein provide for a tip resistant optical testing instrument. In some embodiments, an optical testing instrument configured to rest on a surface is provided. The optical testing instrument may include a shell defining a cavity for receiving a sample tube. The shell may include a bottom shell surface defining at least one support element, wherein the at least one support element may be configured to engage the surface to support the optical testing instrument in a testing position and a translational surface may be configured to engage the surface to support the optical testing instrument in an angled position. In an instance in which the optical testing instrument tilts from the testing position to the angled position, the translational surface may be configured to engage the surface contacting the translational surface to prevent the optical testing instrument from tipping further and allow the optical testing instrument to return to the testing position.

In some embodiments, the at least one support element may be defined radially inward of an edge of the bottom shell surface.

In some cases, a portion of the at least one support element may be recessed in the bottom shell surface.

In some other embodiments, the testing position may define a substantially upright orientation of the optical testing instrument when positioned on the surface, wherein the optical testing instrument may be supported by the at least one support element in the testing position, such that the optical testing instrument may receive a sample.

In some cases, the angled position may define a tilted orientation of the optical testing instrument when positioned on the surface, wherein the optical testing instrument may be configured to be supported by the translational surface in the angled position.

In some embodiments, the at least one support element may further include three legs disposed such that the three legs each protrude from the bottom shell surface. In such an embodiments, the three legs may further include a skid resistant material.

In some cases, the translational surface may further include an annular portion of the bottom shell surface extending circumferentially along an edge of the bottom shell surface.

In yet another embodiment, the bottom shell surface may be circular. In such an embodiment, the at least one support element may further include three legs, wherein a first leg is located along the diameter of the bottom shell surface, and a second and third leg are each located equidistant from the diameter and equidistant from the first leg.

In other cases, the translational surface may further include a plastic material configured to allow the optical testing instrument to slide along the surface while in the angled position.

In any embodiment, the bottom shell surface may further include a charging element such that the optical testing instrument may be further configured to be received by a platform.

In other embodiments, a method of manufacturing an optical testing instrument configured to rest on a surface is provided. The method may include forming a shell where the shell defines a cavity for receiving a sample tube, wherein forming the shell may include forming a bottom shell surface. The bottom shell surface may include at least one support element, wherein the at least one support element may be configured to engage the surface to support the optical testing instrument in a testing position and a translational surface, wherein the translational surface may be configured to engage the surface to support the optical testing instrument in an angled position. In an instance in which the optical testing instrument tilts from the testing position to the angled position, the translational surface may be configured to engage the surface contacting the translational surface to prevent the optical testing instrument from tipping further and allow the optical testing instrument to return to the testing position.

In some embodiments, the at least one support element may be defined radially inward of an edge of the bottom shell surface.

In some cases, a portion of the at least one support element may be recessed in the bottom shell surface.

In some other embodiments, the testing position may define a substantially upright orientation of the optical testing instrument when positioned on the surface, wherein the optical testing instrument may be supported by the at least one support element in the testing position, such that the optical testing instrument may receive a sample.

In some cases, the angled position may define a tilted orientation of the optical testing instrument when positioned on the surface, wherein the optical testing instrument may be configured to be supported by the translational surface in the angled position.

In some embodiments, the at least one support element may further include three legs disposed such that the three legs each protrude from the bottom shell surface. In such an embodiments, the three legs may further include a skid resistant material.

In some cases, the translational surface may further include an annular portion of the bottom shell surface extending circumferentially along an edge of the bottom shell surface.

In yet another embodiment, the bottom shell surface may be circular. In such an embodiment, the at least one support element may further include three legs, wherein a first leg is located along the diameter of the bottom shell surface, and a second and third leg are each located equidistant from the diameter and equidistant from the first leg.

In other cases, the translational surface may further include a plastic material configured to allow the optical testing instrument to slide along the surface while in the angled position.

In any embodiment, the bottom shell surface may further include a charging element such that the optical testing instrument may be further configured to be received by a platform.

BRIEF DESCRIPTION OF THE SEVERAL VIEWS OF THE DRAWINGS

Figure 1:
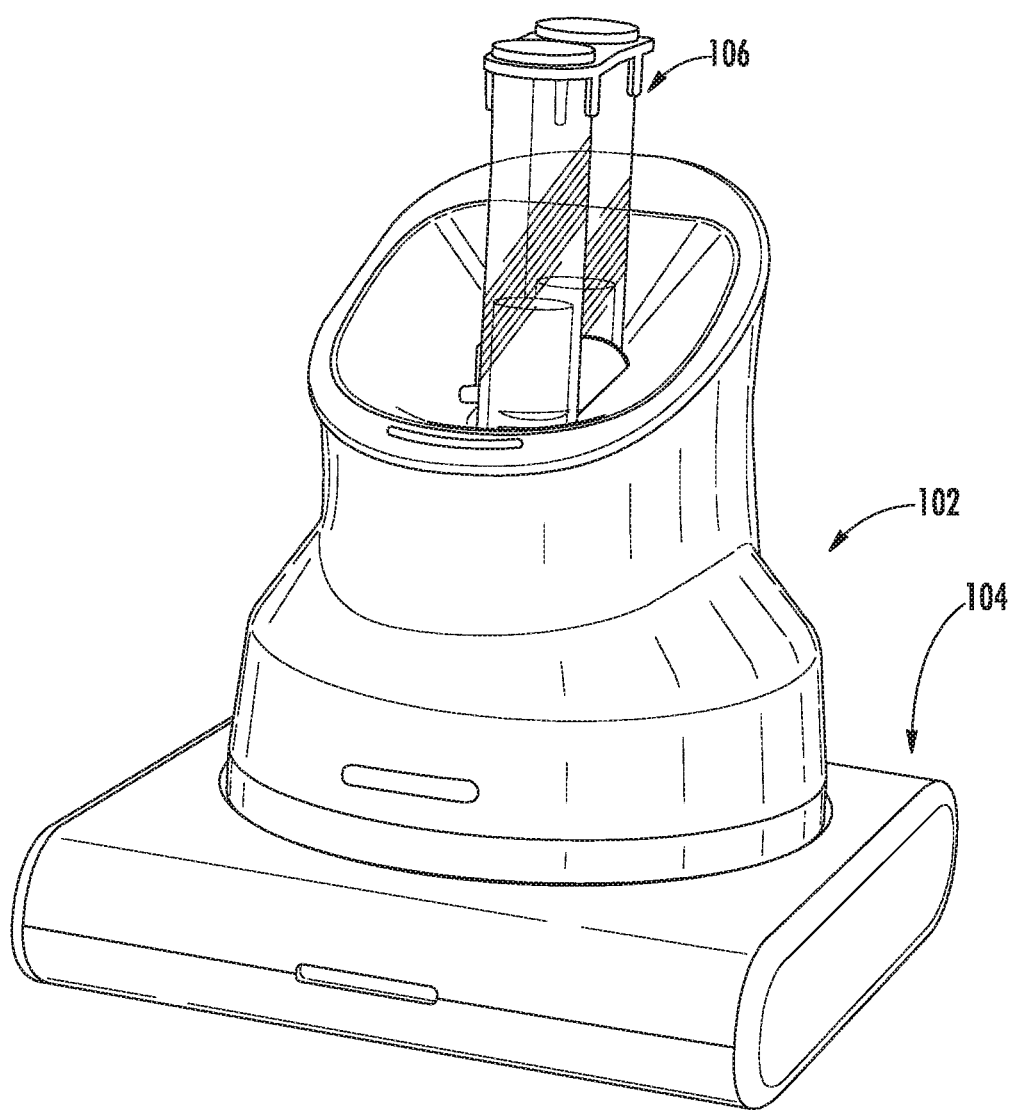
Figure 2:
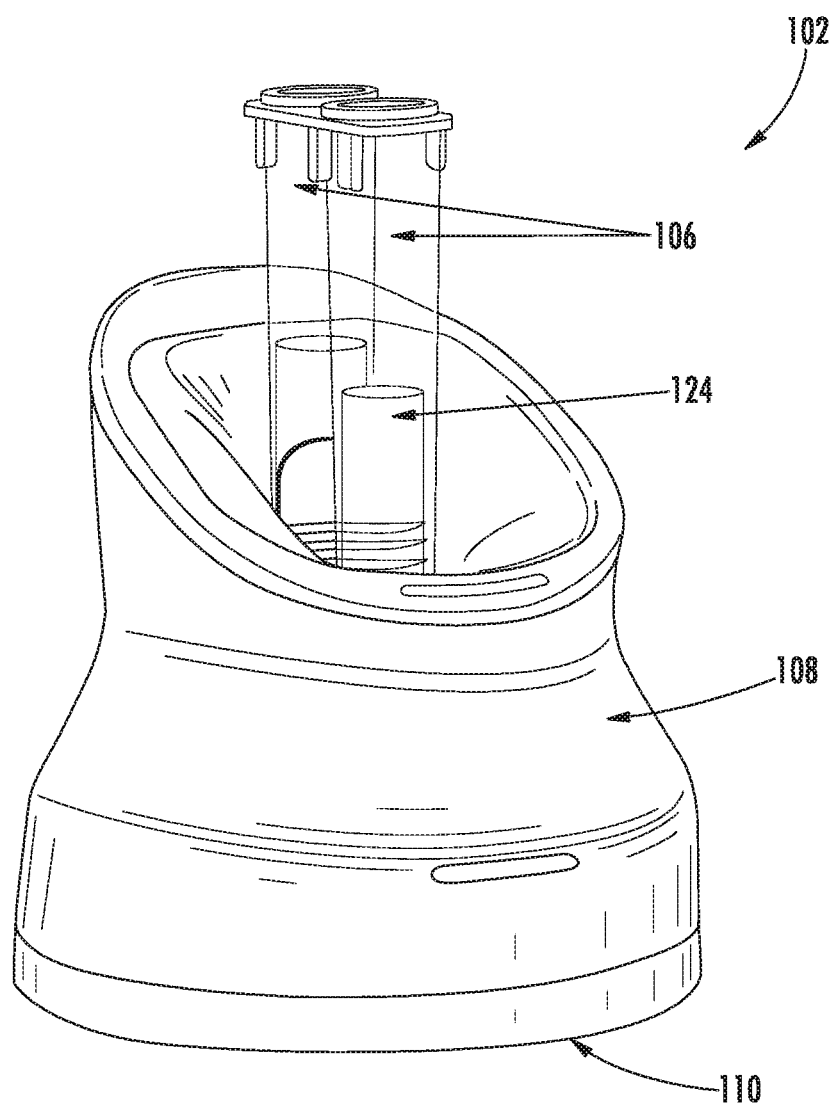
Figure 3:
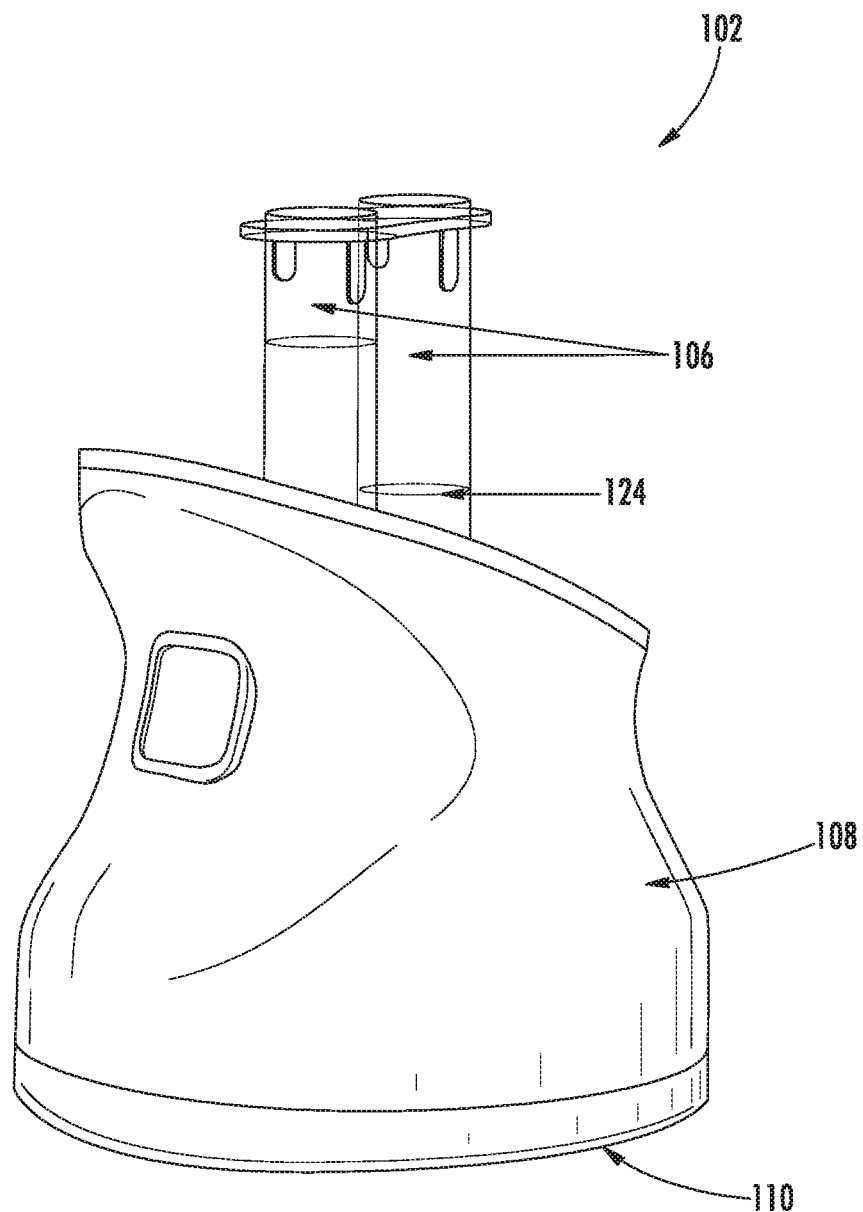
Figure 4:
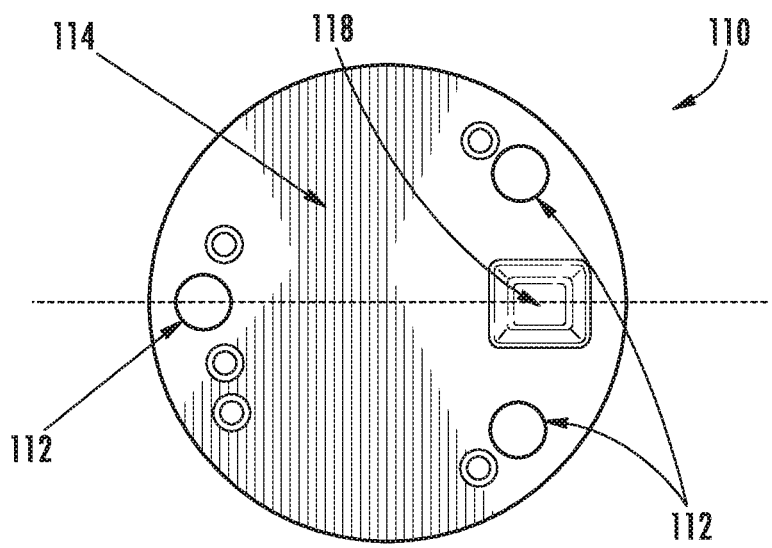
Figure 5:
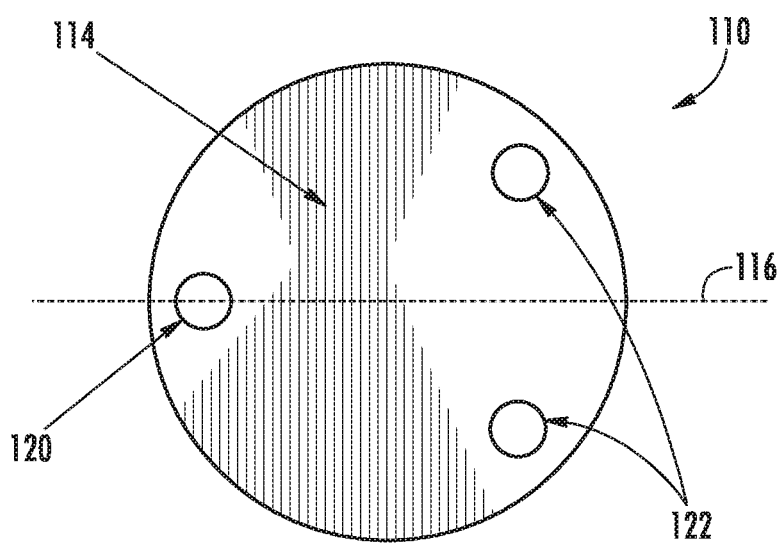
Figure 6:
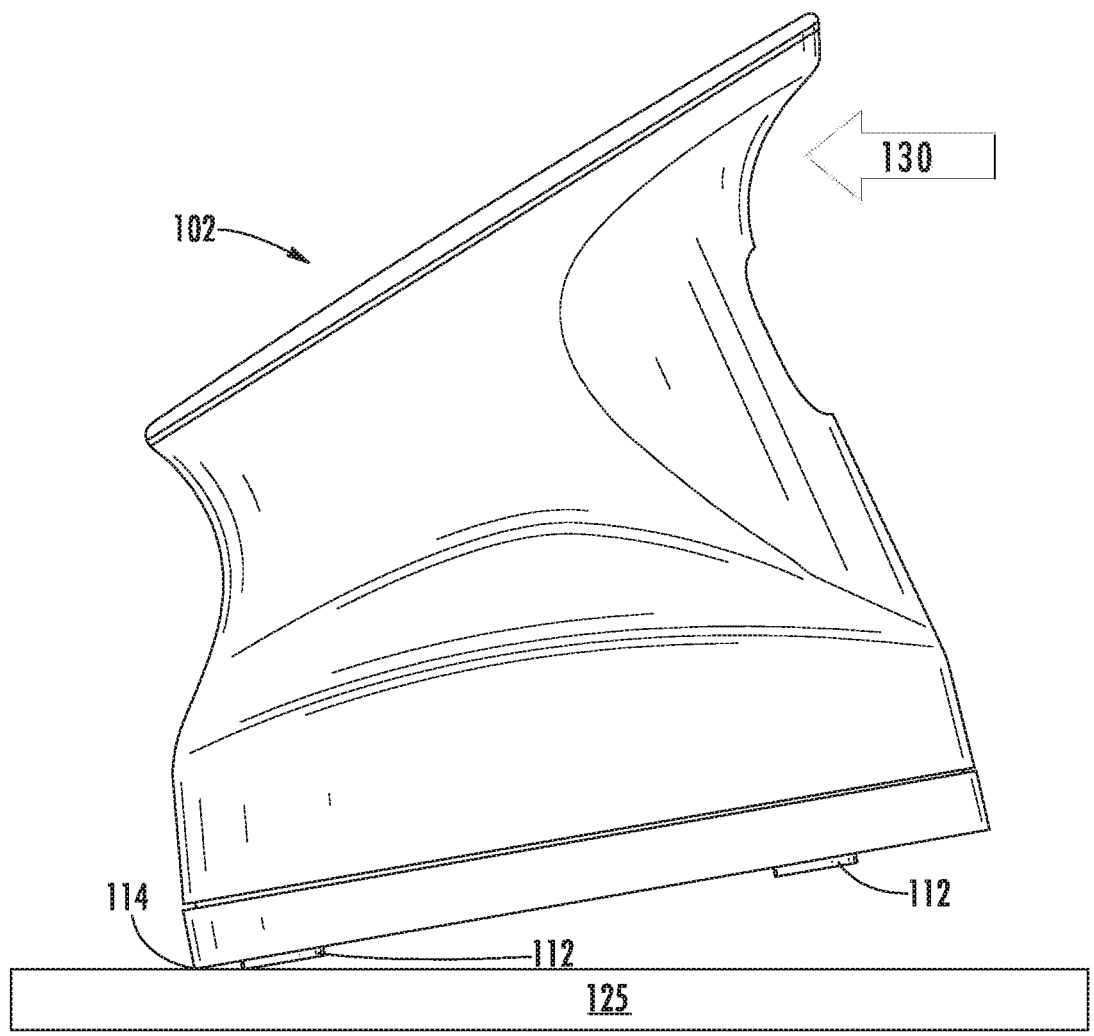

Having thus described the disclosure in general terms, reference will now be made to the accompanying drawings, which are not drawn to scale, and wherein:

FIG. 1 is a perspective view of an optical testing system, according to an example embodiment;

FIG. 2 is a perspective view of an optical testing instrument, according to an example embodiment;

FIG. 3 is rear perspective view of an optical testing instrument of FIG. 2, according to an example embodiment;

FIG. 4 is a bottom view of the optical testing instrument of FIGS. 2-3, according to an example embodiment;

FIG. 5 is a bottom view of the optical testing instrument of FIGS. 2-3, according to an example embodiment; and FIG. 6 is a side view of an optical testing instrument in the angled position according to an example embodiment.

DETAILED DESCRIPTION

The present invention will now be described more fully hereinafter with reference to the accompanying drawings in which some but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The instruments and accompanying methods and systems described herein are directed to an improved optical testing instrument. The optical testing instrument may facilitate optical interrogation of a sample by supporting and positioning the sample in optical alignment with one or more optical density sensors and emitters. In a preferred embodiment, a liquid sample may be held in a sample tube, and the tube may be supported and interrogated by the optical testing instrument. FIG. 1 shows an example optical testing system 100 in accordance with the present invention. In the illustrated embodiment, the optical testing system 100 includes an optical testing instrument 102 (also referred to herein as the "handheld unit") and a platform 104 (also referred to herein as the "base station"). The optical testing instrument 102 may be configured to hold sample tubes 106 for a testing procedure (e.g., optical density testing). The optical testing system 100 may comprise an optical testing instrument 102 (e.g., handheld unit) and a platform 104 (e.g., base station). In some embodiments, the optical testing instrument 102 is battery operated for convenience and flexibility and is configured to perform optical testing procedures. In such an embodiment, the optical testing instrument 102 may transmit data to the platform 104 via Bluetooth® or another wireless or wired protocol. The platform 104 may then be wire or wirelessly connected to a computer for receiving the testing procedure data (e.g., optical density data) in real time. In some embodiments, the optical testing instrument 102 may hold two sample tubes or a fused, dual sample tube. Further details regarding the instrument, its structure, and operation may be found in the in U.S. Provisional Application No. 62/487,796, filed Apr. 20, 2017, and entitled "OPTICAL DENSITY INSTRUMENT AND SYSTEMS AND METHODS USING THE SAME," and in U.S. Provisional Application No. 62/488,450, filed Apr. 21, 2017, and entitled "OPTICAL DENSITY INSTRUMENT AND SYSTEMS AND METHODS USING THE SAME," which applications are incorporated by reference herein in their entireties.

With reference to FIGS. 2-3, the optical testing instrument 102 of FIG. 1 is illustrated. The optical testing instrument 102 may include a shell 108 configured to receive one or more fluid samples 124 (e.g., contained by sample tubes 106) and a bottom shell surface 110. As described above, the shell 108 may be configured to receive one or more sample tubes 106 containing fluid samples 124 (e.g., fluid suspensions of microorganisms for turbidity testing) and may further house various optical density testing instruments including, but not limited to, emitters (e.g., an LED or other light source) and sensors (e.g., photodetectors, photodiodes, or the like). These optical density testing instruments and sensors may be configured such that an emitter may transmit light into a sample tube (e.g., sample tubes 106) such that at least a portion of the transmitted light reflects off of the fluid sample contained therein (e.g., fluid samples 124). The proportion of light reflected to light passing through the sample may be used to determine the turbidity. Various detectors may also be configured to receive at least a portion of the transmitted light reflected by the fluid samples 124. The orientation of the various emitters and detectors housed within the shell 108 may be positioned such that various optical testing procedures may be conducted. Further details regarding the operation of the emitters and detectors, including calibration, zeroing, and data collection, in addition to various optical testing procedures, may be found in U.S. Provisional Application No. 62/487,736, filed Apr. 20, 2017, and entitled "METHOD, APPARATUS, AND COMPUTER PROGRAM PRODUCT FOR CONTROLLING COMPONENTS OF A DETECTION DEVICE," which application is incorporated by reference herein in its entirety.

The optical testing instrument 102 may define a bottom shell surface 110. As will be described more fully hereinafter, the bottom shell surface 110 may be configured to provide support for the optical testing instrument 102. In some embodiments, the optical testing instrument 102 may be configured to rest upon a substantially flat surface (e.g., desktop or the like) during both operation (e.g., performing a testing procedure) as well as during rest (e.g., between testing procedures).

As shown in FIGS. 2-3, the preferred orientation and operational orientation of the optical testing instrument 102 is in an upright testing position as shown. When the optical testing instrument 102 is properly oriented in a testing position, one or more sample tubes 106 containing fluid sample 124 may be placed substantially vertically in the shell 102 (e.g., via a cavity defined therein). Although described herein with regard to a substantially vertical orientation, the present disclosure contemplates that the testing position of the optical testing instrument may be oriented at any position so long as a liquid sample may be properly housed therein such that optical testing procedure may be properly conducted and in which the support elements (e.g., support elements 112 shown in FIG. 5) are planted on the surface that supports the optical testing instrument. In order to resist or otherwise prevent the tipping over of the optical testing instrument, the bottom shell surface 110 may be configured as shown in FIGS. 4-5.

With reference to FIGS. 4-5, a bottom view of a bottom shell surface 110 is illustrated. The bottom shell surface 110 may define at least one support element 112 and a translational surface 114. The at least one support element 112 may, in some embodiment, comprise feet (e.g., protrusions, pedestals, stands, or other supportive elements) configured to support the optical testing instrument 102 in a testing position (e.g., an upright orientation in which the support elements 112 are contacting a surface as show in FIGS. 2-3). As shown in FIGS. 4-5, in a preferred embodiment, the bottom shell surface 110 may define three support elements 112 (e.g., legs 120, 122 shown in FIG. 5) disposed such that the three support elements each protrude in a direction substantially perpendicular to the bottom shell surface 110. In some embodiments, the support elements 112 may protrude from the bottom shell surface 110 at an acute angle to the bottom shell surface 110 with a non-zero perpendicular component dimension of the support elements 112 (e.g., the support elements may be angled while still protruding from the bottom shell surface 110). As would be understood by one of ordinary skill in the art in light of the present disclosure, the component of the protrusion of each of the three support elements 112 perpendicular to the bottom shell surface 110 may raise the optical testing instrument 102 such that the translational surface 114, described hereinafter, does not contact a supporting surface (e.g., a substantially flat desktop or the like) when in the testing position.

In some embodiments, the support elements 112 may comprise a plurality of individual elements. In some other embodiments, the at least one support element may comprise a single, large support element (e.g., a flat disk). In some embodiments, the at least one support element may comprise two or more support elements. In some embodiments, the at least one support element may comprise three or more support elements. In some embodiments, the at least one support element may comprise four or more support elements. In some embodiments, the at least one support element may comprise five or more support elements. In some embodiments, the at least one support element may comprise six or more support elements.

The support elements 112 may, in some embodiments, be configured such that a portion of the at least one support element 112 (e.g., three protruding feet) is recessed in the bottom shell surface 110. In some embodiments, the support elements 112 may define feet (e.g., three feet 120, 122 shown in FIG. 5) each having a height of approximately $\frac{1}{8}^{th}$ inches. In such an embodiment, the $\frac{1}{8}^{th}$ inch feet may each be recessed approximately $\frac{1}{16}^{th}$ inches within the bottom shell surface 110. The use of a recesses as described herein may function, in some embodiments, to allow the translational surface 114 to more easily contact a support surface when the optical testing instrument in oriented in an angled position (e.g., sliding or otherwise translating across a support surface as shown in FIG. 6). Although described and illustrated in FIGS. 4-5 with three feet (e.g., support elements 112), the present disclosure contemplates that any number of support elements having any cross-sectional shape may be utilized by the present invention. Further, although the bottom shell surface 110 is illustrated with a circular cross-sectional shape, the present disclosure contemplates that any cross-sectional shape may be equally applicable to the proposed invention.

In some embodiments, the support elements 112 may comprise a non-skid or skid resistant material. In such an embodiment, the support element may be comprised of a material that resists translational movement. By way of example, the support elements 112 may be manufactured from a rubber material such that, when the optical testing instrument 102 is oriented in a testing position, the support elements 112 (e.g., contacting a support surface) may resist the translational movement of the optical testing instrument 102, for example, via friction with the surface on which the optical testing instrument is resting. By way of a more particular example, if a user applies a force to the optical testing instrument 102 while oriented in a testing position, the skid resistant support elements 112 may resist the applied force and further prevent sliding of the optical testing instrument 102.

In some embodiments, the support elements 112 may define a coefficient of friction that is greater than a coefficient of friction of the translational surface 114. In such embodiments, the optical testing instrument 102 may grip the surface (e.g., a table or lab bench) with the support elements 112 and cause the instrument 102 to tend to tip when pushed. In some instances, where the instrument 102 is pushed at or below a predetermined height on the shell 108 or with a sufficiently high angle of attack, the support elements 112 may slide.

In some embodiments, as shown in FIG. 5, the support elements 112 may be positioned on the bottom shell surface 110 such that a first leg 120 is located along a diametric line 116 of the circular bottom shell surface 110, and a second and third leg 122 are each located equidistance from the diametric line 116 and the first leg 120. As shown in FIG. 5, this positioning of the support elements 112, along with recessing the support elements a portion into the bottom shell surface 110 may be combined in an embodiment of the present disclosure. In some embodiments, the support elements may be circumferentially equidistant from each adjacent support element and each support element may be equidistant from a center of the bottom surface 110. Additionally, in some embodiments as shown in FIGS. 4-5, the support elements 112 may be spaced a distance from the outer edge of the bottom shell surface 110. Particularly, the support elements 112 may be disposed on a concentric circle having a diameter that is less than the outer diameter of the bottom shell surface 110. As described below, in such an embodiment, the translational surface 114 may be positioned as an annular portion of the bottom shell surface extending radially outward from the support elements 112 to the outer edge of the bottom shell surface 110.

The translational surface may be configured with a lower coefficient of friction to allow the optical testing instrument to slide when supported by the translational surface (e.g., when the optical testing instrument is tipped as described herein. As depicted in FIGS. 4-5, the translational surface 114 of the bottom shell surface 110 may, in some embodiments, comprise a substantially flat surface. As described above, in an instance in which the optical testing instrument 102 is oriented in a testing position, the translational surface 114 may be positioned substantially parallel to the support surface (e.g., a substantially flat table, workbench, desktop or the like). Also described above, in an embodiment in which the support elements 112 are approximately $\frac{1}{8}^{th}$ inches in total height and recessed approximately $\frac{1}{16}^{th}$ inches into the bottom shell surface 110, the translational surface 114 may be raised $\frac{1}{16}^{th}$ inches above the support surface. In some embodiments, the translational surface 114 may be a section or portion of the bottom shell surface 110. In some embodiments, the translational surface 114 may be a contiguous section or portion of the bottom shell surface 110. In some embodiments, all of the bottom shell surface 110 may have the lower friction coefficient than the support elements 112, and the portion of the bottom shell surface 110 that contacts the support surface may be considered the translational surface. In some embodiments, the translational surface 114 may be defined as an annular portion of the bottom shell surface 110 extending circumferentially around an edge of the bottom shell surface 110. By a more particular example, the translational surface 114 may be defined by the bottom shell surface 110 as an annular portion of the bottom shell surface extending radially outward from the support elements 112 to an edge of the bottom shell surface 110.

One of ordinary skill in the art will appreciate, in light of this disclosure, that the support elements 112 and bottom shell surface 110 may take many shapes and forms so long as the instrument 102 is permitted to translate on the translational surface 114 when tipped, rather than tipping completely over. To facilitate the translation, a portion of the translational surface 114 need only be positioned opposite the direction of force from the support elements 112 that form the fulcrum of the instrument. Said differently, when the instrument 102 is tipped about a pivot axis on one or more of the support elements 112, the translational support surface 114 is pivoted into contact with the support surface. In many instances, this means that portions of the translational surface 114 are positioned radially outward of the support elements 112. In some further embodiments, the translational support surface 114 engages the support surface before the instrument can tip past the point that its center of gravity carries the instrument the rest of the way over.

Optical Testing Instrument Operation

As will be understood by the above description of the bottom shell surface 110 of the optical testing instrument 102, the optical testing instrument 102 may be operationally oriented in a testing position (e.g., an upright, operational position). As described above, the testing position may be, in some embodiments, the preferred and/or resting orientation of the optical testing device 102 such that the optical testing device 102 may receive a sample tube 106 and corresponding fluid samples 124. When oriented in a testing position, the optical testing instrument 102 may be supported by the support elements 112. However, in an instance in which a sufficient force (e.g., force 130) is applied to the optical testing instrument 102 such that the optical testing instrument tips and contacts the translational surface 114 against the support surface (e.g., the support surface 125 shown in FIG. 6), the optical testing instrument 102 may be oriented in an angled position as shown in FIG. 6. By way of example, when the optical testing instrument 102 is applied with a sufficient force to begin to tip over, the translational surface 114 (e.g., at a position radially outward from the support elements 112) may contact the support surface and one or more of the support elements 112 may no longer contact the support surface (e.g., support elements 112 opposite the direction of tilt may be lifted off of the support surface) or may only loosely contact the support surface (e.g., with all or most of the downward force removed. If a sufficiently strong tipping force is applied to the instrument 102, the support elements 112 may leave the support surface entirely. In either embodiment, the optical testing instrument may then be oriented in an angled position and may translate (e.g., by sliding) some distance along the support surface through contact with the translational surface 114. In this manner, while the support elements 112 prevent the optical testing instrument 102 from sliding about the support surface when in the testing position, the translational surface 114, having a lower coefficient of friction than the support elements, prohibits the instrument from tipping entirely over by translating across the support surface instead. The effect of the disparate frictional coefficients of the translational surface 114 and support elements 112 is that the greater the force applied to the optical testing instrument 102, the less surface area of the support elements 112 contacts the support surface (e.g., a bench or table) and the more likely the optical testing instrument is to slide along the support surface resting on the translational surface.

With reference to FIG. 6, in an instance in which the optical testing instrument 102 is oriented in an angled position, the translational surface 114 may at least partially support the optical testing instrument 102 on the support surface 125. By way of continued example, once the optical testing instrument is located in an angled position, the translational surface 114 (e.g., an annular portion extending along the edge of the bottom shell surface 110) may contact the support surface. As described above, in some embodiments, the translational surface 114 may comprise a smooth plastic material such that the optical testing instrument translates (e.g., slides) along the support surface when in an angled position. By way of a more particular example, when the optical testing instrument 102, whether accidently or intentionally, is forced (e.g., pushed, hit, or the like with a force 130) from a testing position (e.g., upright orientation) to an angled position (e.g., translational surface contacting the support surface), the optical testing instrument 102 may slide along the support surface 125 (via the assistance of the translational surface 114), and then return to a testing position. As described herein, the translational surface 114 operates to partially allow the translational movement of the optical testing instrument 102, when pushed, such that the optical testing instrument 102 does not topple or tip over, but instead may tip back from the angled position to return to the testing position after sliding to dissipate the force applied to the instrument. Although described herein as a general angled position, the present disclosure contemplates that the angled position may encompass any angular displacement experienced by the optical testing instrument 102. For example, the angled position may comprise any position at which the translational surface 114 contacts the table surface 125. In some embodiments, the translational surface 114 may refer to a portion of the bottom surface 110 that contacts the support surface.

In some embodiments, the translation of the optical testing instrument 102 may begin when the tipping force or inertia of the instrument overcomes the static friction between the instrument (e.g., including the combination of translational surface 114 and support element 112 surfaces currently touching the support surface) and the support surface 125. For example, if the support elements 112 have a higher coefficient of friction than the translational surface 114, the greater the portion of the instrument's weight that is transferred to the translational surface 114, the more likely the instrument is to slide. In this manner, the instrument 102 may begin translating while both the translational surface 114 and one or more of the support elements 112 are in contact with the support surface 125. In such embodiments, as the instrument 102 tips, a greater and greater portion of the weight of the instrument is transferred to the translational surface 114, thus gradually lowering the frictional resistance between the instrument and the support surface 125. Once the lateral force between the instrument 102 and the support surface 125 overcomes the decreasing frictional resistance, the instrument begins to translate. The stability of the tool may depend upon the height of the support elements 112, the coefficients of friction of the support elements 112 and the translational element 114, the distance between the support elements 112 and the contact point of the translational element 114 (e.g., the point, proximate the edge of the bottom shell surface 110, at which the translational surface 114 contacts the support surface 125), the center of gravity of the instrument 102, the width of the instrument 102, the shape of the bottom shell surface 110, and the properties of the support surface 125.

In some embodiments, for example as shown in FIG. 5, the instrument 102 may pivot about two or more support elements 112 about a common contact axis extending therebetween. In such embodiments, the instrument 102 may pivot about the two or more support elements 112 until the translational surface 114 contacts the support surface.

In some embodiments, the optical testing instrument may further define an electrical connector 118 (e.g., floating pin connector or the like) such that the optical testing instrument 102 may be received by a platform 104. By way of example, in some embodiments, as shown in FIG. 1, the optical testing instrument 102 may be configured to be received by or otherwise electrically connected with a platform 104. As described above, this electrical connection may allow electrical communication between the optical testing instrument 102 and the platform 104 such that testing procedure data (e.g., gathered by the optical testing instrument 102 conducting a testing procedure) may be transmitted from the optical testing instrument 102 to the platform 104. Similarly, in some embodiments, the electrical connector 118 may be configured to allow the optical testing instrument 102 (e.g., handheld unit) to be recharged (via a battery system or the like).

The present disclosure contemplates that the present invention may be created from any suitable material known in the art (e.g., plastics, polymers, ceramics, and the like). By way of example, the optical testing instrument 102 may be created by an injection molding process such that the shell 108 and bottom shell surface 110 are molded by the injection molding process. In such an example, the shell 108 and bottom shell surface 110 may be comprised of a smooth plastic material (e.g., any plastic or material with a low coefficient of friction) such that the translational surface 114 may support the optical testing instrument 102 while sliding along a support surface. In such an embodiment, the support elements 112 may equally be created by an injection molding procedure such that the support elements 112 are integral to the bottom shell surface 110. The support elements 112 created from an injection molding procedure may then, in some embodiments, be made of (such as in the case of insertion molding), or coated with a skid resistant material (e.g., rubber or any suitable material with a higher coefficient of friction) such that the support elements 112 may support the optical testing instrument 102 when oriented in a testing position. Although the shell 108, including bottom shell surface 110 and translational surface 114, may be described as a single, molded piece of material, any portion or sub-portion of the shell 108 may be separately formed or attached without departing from the scope of this disclosure.

In an alternative embodiment, the shell 108 and bottom shell surface 110 may be defined by an injection molding process, but the support elements 112 may be separately affixed to the bottom shell surface 110. In such an embodiment, the support elements 112 may comprise a skid resistant material or may be coated in a skid resistant material. Although described above in reference to an injection molding process, the present disclosure contemplates that any suitable manufacturing process (e.g., extrusion, machining, 3-D printing, or the like) may be utilized to create any of the elements described herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In some embodiments, the principles discussed herein may be applied to any object or device that may tip, such that the components and functionalities described herein are not limited to the specific context in which they are described. Although specific terms are employed herein, they are used in a generic and descriptive sense only and not for purposes of limitation.

The invention claimed is:

1. A handheld optical testing instrument configured to rest on a surface and shaped to be gripped by a user, the optical testing instrument comprising:
    a shell defining a cavity for receiving a sample tube, the cavity is configured to support the sample tube in an upright position in an instance in which the optical testing instrument is in a testing position, wherein the cavity defines an open end, the shell comprising a bottom shell surface, wherein the bottom shell surface comprises:

at least one support element, wherein the at least one support element is configured to engage the surface to support the optical testing instrument in a testing position; and a translational surface configured to engage the surface to support the optical testing instrument in an angled position, wherein at least one emitter and at least one sensor are housed within the shell, the at least one emitter operable to transmit light into the sample tube and the at least one sensor operable to receive at least a portion of the transmitted light, wherein the shell is shaped to be gripped by a user in a circumferential direction defined about a longitudinal axis of the cavity such that the user can hold the sample tube upright within the optical testing instrument during handheld operation, the longitudinal axis of the cavity extending through the open end and configured to be defined parallel to a longitudinal axis of the sample tube, wherein in an instance in which the optical testing instrument receives at least one lateral force, the optical testing instrument is arranged to tilt from the testing position to the angled position to cause the translational surface to engage and slide relative to the surface to prevent the optical testing instrument from tipping past a point where the optical testing instrument tips over such that the optical testing instrument is arranged to return to the testing position in an instance in which the at least one lateral force is removed, wherein, in both the testing position and the angled position, a center of gravity of the optical testing instrument is disposed above points on the surface that are radially inward of an engagement point of the translational surface that engages the surface, and wherein a coefficient of friction of the translational surface is less than a coefficient of friction of the at least one support element at a location where the at least one support element engages the surface.

2. The optical testing instrument according to claim 1, wherein the at least one support element is defined radially inward of an edge of the bottom shell surface.

3. The optical testing instrument according to claim 1, wherein a portion of the at least one support element is recessed in the bottom shell surface.

4. The optical testing instrument according to claim 1, wherein the testing position defines a substantially upright orientation of the optical testing instrument when positioned on the surface, wherein the optical testing instrument is supported by the at least one support element in the testing position, such that the optical testing instrument may receive a sample.

5. The optical testing instrument according to claim 1, wherein the angled position defines a tilted orientation of the optical testing instrument when positioned on the surface, wherein the optical testing instrument is configured to be supported by the translational surface in the angled position.

6. The optical testing instrument according to claim 1, wherein the at least one support element further comprises three legs disposed such that the three legs each protrude from the bottom shell surface.

7. The optical testing instrument according to claim 6, wherein the three legs further comprise a skid resistant material.

8. The optical testing instrument according to claim 1, wherein the translational surface further comprises an annular portion of the bottom shell surface extending circumferentially along an edge of the bottom shell surface.

9. The optical testing instrument according to claim 1, wherein the bottom shell surface is circular.

10. The optical testing instrument according to claim 9, wherein the at least one support element further comprises three legs, wherein a first leg is located along the diameter of the bottom shell surface, and a second and third leg are each located equidistant from the diameter and equidistant from the first leg.

11. The optical testing instrument according to claim 1, wherein the translational surface further comprises a plastic material configured to allow the optical testing instrument to slide along the surface while in the angled position.

12. The optical test instrument according to claim 7, wherein the three legs are equidistant from the edge of the bottom shell surface.

13. The optical test instrument according to claim 9, wherein the translational surface is circular.

14. The optical test instrument according to claim 1, further comprising a battery and a wireless transmitter, wherein the optical test instrument is configured to wirelessly collect and transmit optical density data in real time while being held by a user.

15. The optical test instrument according to claim 1, wherein the shell defines an hourglass shape shaped to be gripped by a user.

16. A method of manufacturing a handheld optical testing instrument configured to rest on a surface and shaped to be gripped by a user, the method comprising:

forming a shell, the shell defining a cavity for receiving a sample tube, wherein the cavity is configured to support the sample tube in an upright position in an instance in which the optical testing instrument is in a testing position, wherein the cavity defines an open end, wherein forming the shell comprises forming a bottom shell surface, wherein the bottom shell surface comprises:

at least one support element, wherein the at least one support element is configured to engage the surface to support the optical testing instrument in the testing position; and a translational surface, wherein the translational surface is configured to engage the surface to support the optical testing instrument in an angled position, wherein at least one emitter and at least one sensor are housed within the shell, the at least one emitter operable to transmit light into the sample tube and the at least one sensor operable to receive at least a portion of the transmitted light;

wherein the shell is shaped to be gripped by a user in a circumferential direction defined about a longitudinal axis of the cavity such that the user can hold the sample tube upright within the optical testing instrument during handheld operation, the longitudinal axis of the cavity extending through the open end and configured to be defined parallel to a longitudinal axis of the sample tube, wherein in an instance in which the optical testing instrument receives at least one lateral force, the optical testing instrument is arranged to tilt from the testing position to the angled position to cause the translational surface to engage and slide relative to the surface to prevent the optical testing instrument from tipping past a point where the optical testing instrument tips over such that the optical testing instrument is arranged to return to the testing position in an instance in which the at least one lateral force is removed, wherein, in both the testing position and the angled position, a center of gravity of the optical testing instrument is disposed above points on the surface that are radially inward of an engagement point of the translational surface that engages the surface, and wherein a coefficient of friction of the translational surface is less than a coefficient of friction of the at least one support element at a location where the at least one support element engages the surface.

17. The method according to claim 16, wherein the at least one support element is defined radially inward of an edge of the bottom shell surface.

18. The method according to claim 16, wherein a portion of the at least one support element is attached to the bottom shell surface in a recess in the bottom shell surface.

19. The method according to claim 16, wherein the at least one support element further comprises three legs disposed such that the three legs each protrude from the bottom shell surface.

20. The method according to claim 19, wherein the three legs further comprise a skid resistant material.

21. The method according to claim 16, wherein the translational surface further comprises an annular portion of the bottom shell surface extending circumferentially along an edge of the bottom shell surface.

22. The method according to claim 16, wherein the bottom shell surface is circular.

23. The method according to claim 16, wherein the at least one support element further comprises three legs, wherein a first leg is located along the diameter of the circular bottom shell surface, and a second and third leg are each located equidistant from the diameter and equidistant from the first leg.

24. The method according to claim 16, wherein the translational surface further comprises a plastic material configured to allow the optical testing instrument to slide along the surface while in the angled position.

* * * * *